(12) United States Patent
Hopkins et al.

(10) Patent No.: US 6,652,583 B2
(45) Date of Patent: Nov. 25, 2003

(54) CARDIAC VALVE REPLACEMENT

(75) Inventors: Richard A. Hopkins, Providence, RI (US); Diane Hoffman-Kim, Providence, RI (US)

(73) Assignee: Rhode Island Hospital, Providence, RI (US)

( * ) Notice: Subject to any disclaimer, the term of this patent is extended or adjusted under 35 U.S.C. 154(b) by 0 days.

(21) Appl. No.: 09/828,768

(22) Filed: Apr. 9, 2001

(65) Prior Publication Data

US 2001/0051824 A1 Dec. 13, 2001

Related U.S. Application Data

(60) Provisional application No. 60/195,673, filed on Apr. 7, 2000.

(51) Int. Cl.$^7$ .................................................. A61F 2/24

(52) U.S. Cl. ................................................. 623/2.13

(58) Field of Search ........................... 623/2.12–2.19, 623/1.24, 1.26, 917, 918, 925

(56) References Cited

U.S. PATENT DOCUMENTS

| | | | |
|---|---|---|---|
| 4,707,998 A | 11/1987 | Linner et al. | 62/349 |
| 4,745,771 A | 5/1988 | Linner et al. | 62/264 |
| 4,807,442 A | 2/1989 | Linner et al. | 62/55.5 |
| 4,865,871 A | 9/1989 | Livesay et al. | 427/4 |
| 4,963,489 A | 10/1990 | Naughton et al. | 435/240.1 |
| 4,964,280 A | 10/1990 | Piunno et al. | 62/78 |
| 5,044,165 A | 9/1991 | Linner et al. | 62/55.5 |

(List continued on next page.)

FOREIGN PATENT DOCUMENTS

| | | |
|---|---|---|
| WO | WO 96/03093 | 2/1996 |
| WO | WO 96/08213 | 3/1996 |

OTHER PUBLICATIONS

GENBANK Accession No. M27968 or J04513.
GENBANK Accession No. AF092127, AF092125, or M32977.
GENBANK Accession No. M26179.
GENBANK Accession No. L24121 or U31518.
GENBANK Accession No. J04431.
GENBANK Accession No. U06669.
GENBANK Accession No. M33216.
GENBANK Accession No. M20642.
GENBANK Accession No. X68969.
Gimbrone, M.A., 1976, Culture of vascular endothelium, Chapter 1 in Spaet, T. (ed.) Progress in hemostasis and thrombosis. vol. III. Grune and Stratton, Inc., pp. 1–28.
Grinnell et al., "Collagen Processing, Crosslinking, and Fibril Bundle Assembly in Matrix Produced by Fibroblasts in Long–Term Cultures Supplemented with Ascorbic Acid," 1989, Exp. Cell Res. 181:183–191.
Harris et al., "Silicone Rubber Substrata: A New Wrinkle in the Study of Cell Locomotion," 1980, Science 208:177.
Hilbert et al., "Allograft heart valves: the role of apoptosis mediated cell loss," Journal of Thoracis and Cariovcascular Surgery, 117 (3): 454–462, 1999.
Khouw et al., "TGF–β and bFGF affect the differentiation of proliferating porcine fibroblasts into myofibroblasts in vitro," 1999, Biomaterials 20:1815–1822.
Messier et al., "Dual structural and functional henotypes of porcine aortic valve interstitial population: characteristics of the leaflet myofibroblast," Journal of Surgical Research, 57:1–21, 1994.

(List continued on next page.)

*Primary Examiner*—David H. Willse
*Assistant Examiner*—Javier G. Blanco
(74) *Attorney, Agent, or Firm*—Ingrid A. Beattie; Mintz, Levin, Cohn, Ferris, Glovsky and Popeo, P.C.

(57) ABSTRACT

The invention provides a replacement heart valve which contains an acellular matrix as a structural scaffold. The scaffold is seeded with isolated myofibroblasts and/or endothelial cells prior to implantation into a recipient mammal.

13 Claims, 6 Drawing Sheets

U.S. PATENT DOCUMENTS

| | | | |
|---|---|---|---|
| 5,154,007 A | 10/1992 | Piunno et al. | 34/5 |
| 5,266,480 A | 11/1993 | Naughton et al. | 435/240.243 |
| 5,275,954 A | 1/1994 | Wolfinbarger et al. | 436/74 |
| 5,336,616 A | 8/1994 | Livesey et al. | 435/240.2 |
| 5,364,756 A | 11/1994 | Livesey et al. | 435/2 |
| 5,460,939 A | 10/1995 | Hansbrough et al. | 435/1.1 |
| 5,531,791 A | 7/1996 | Wolfinbarger | 623/16 |
| 5,556,379 A | 9/1996 | Wolfinbarger | 604/49 |
| 5,622,867 A | 4/1997 | Livesey et al. | 436/18 |
| 5,714,582 A | 2/1998 | Wolfinbarger | 530/356 |
| 5,770,193 A | 6/1998 | Vacanti et al. | 424/93.7 |
| 5,770,417 A | 6/1998 | Vacanti et al. | 435/180 |
| 5,780,295 A | 7/1998 | Livesey et al. | 435/307 |
| 5,797,871 A | 8/1998 | Wolfinbarger | 604/49 |
| 5,820,581 A | 10/1998 | Wolfinbarger | 604/49 |
| 5,842,182 A | 11/1998 | Bonner et al. | 705/32 |
| 5,843,182 A * | 12/1998 | Goldstein | 623/2 |
| 5,855,610 A | 1/1999 | Vacanti et al. | 623/11 |
| 5,879,876 A | 3/1999 | Wolfinbarger et al. | 435/1.2 |
| 5,899,937 A * | 5/1999 | Goldstein et al. | 623/2 |
| 5,919,614 A | 7/1999 | Livesey et al. | 435/2 |
| 5,963,489 A | 10/1999 | Kirihata et al. | 365/200 |
| 5,976,104 A | 11/1999 | Wolfinbarger | 604/49 |
| 5,977,034 A | 11/1999 | Wolfinbarger | 510/109 |
| 5,977,432 A | 11/1999 | Wolfinbarger | 623/16 |
| 5,984,959 A | 11/1999 | Robertson et al. | 623/2 |
| 6,024,735 A | 2/2000 | Wolfinbarger | 604/500 |
| 6,189,537 B1 | 2/2001 | Wolfinbarger | 128/898 |
| 6,194,136 B1 | 2/2001 | Livesey et al. | 453/1.3 |
| 6,200,347 B1 | 3/2001 | Anderson et al. | 623/16.11 |
| 6,221,669 B1 | 4/2001 | Livesey et al. | 436/18 |
| 6,432,712 B1 * | 8/2002 | Wolfinbarger, Jr. | 435/395 |

OTHER PUBLICATIONS

Messier et al., Interstitial Cellular and Matrix Restoration of Cardiac Valves After Cryopreservation, 1999, J. Thoracis and Cardiovasc. Surg. 118:36–41.

Omstead et al., "Voluntary Guidance for the Development of Tissue–Engineered Products," Tissue Engineering, 4(3):239–266, 1998.

Reynaud et al., "Comparative Functional Study of the Lysyl Oxidase Promoter in Fibroblasts, Ras–Transformed Fibroblasts, Myofibroblasts and Smooth Muscle Cells," 1999, Cellular and Molecular Biol. 45:1237–1247.

Tajima et al., "Regulation of Collagen Synthesis by Ascorbic Acid. Ascorbic Acid Increases Type I Procollagen mRNA," 1982, Biochem. Biophys. Res. Commun. 106:632–7.

* cited by examiner

CARDIAC VALVE REPLACEMENT

This application claims priority to provisional patent application U.S. Ser. No. 60/195,673 filed Apr. 4, 2000, the entire contents of which are hereby incorporated by reference.

BACKGROUND

This invention relates to cardiac valve replacement.

Cardiac valve diseases are prevalent clinical problems, usually requiring prosthetic replacement. Valves can become diseased or damaged from a variety of causes. Congenital defects may result in abnormally formed valves. Infections such as rheumatic fever and bacterial endocarditis can lead to valve damage.

The first prosthetic valvular device was implanted in 1952, and a variety of mechanical, bioprosthetic, and homograft valves are presently in use. Thromboembolic events and sudden structural failure are problems associated with traditional mechanical valves. Bioprosthetic xenograft replacement valves have been developed to reduce the risk of such problems. Xenograft valves are typically porcine or bovine. However, such valves are limited in their durability, as calcification and fibrotic sheath formation often lead to stenosis and regurgitation, with a 40% reoperation rate 8–10 years after implantation. Homograft valve transplants are limited by immune and inflammatory recipient responses, limited donor cell viability, and complex matrix issues resulting in degradation of mechanical performance properties.

SUMMARY

The invention provides an improved replacement cardiac valve. The bioprosthetic heart valve contains an acellular matrix as a structural scaffold and isolated myofibroblasts. The acellular matrix is preferably an acellular homograft, an acellular xenograft, or a synthetic matrix. The matrix is contacted with isolated myofibroblasts, which are allowed to cellularize the matrix. The myofibroblasts are resistant to dedifferentiation during culture prior to implantation and after implantation into a recipient individual. At least 60% of the total collagen produced by the myofibroblasts is type I collagen. Preferably, the myofibroblasts produce at least 2-fold more type I collagen compared to type III collagen. Reduced type III collagen production is critical to minimizing scar tissue formation in the replacement valve recipient. Accordingly, less than 25%, more preferably less than 20%, and most preferably less than 15% of total collagen production by valve myofibroblasts is type III collagen.

In addition to increased type I collagen production, the myofibroblasts secrete extracellular matrix components, including but not limited to, fibronectin, elastin, and glycosaminoglycans, such as chondroitin sulfate or hyaluronic acid. The myofibroblast cells are cultured in the presence of factors which inhibit dedifferentiation. The cells are cultured in the presence or absence of an acellular matrix or scaffold. For example, the cells are maintained in an endothelial cell-conditioned media, or grown in the presence of endothelial cells. The two cell types may be in direct contact with one another, e.g., in a coculture, or separated by a membrane which allows diffusion of soluble factors but prevents cell-to-cell contact.

The term "isolated" used in reference to a particular cell type, e.g., a myofibroblast or endothelial cell, means that the cell is substantially free of other cell types or compositions with which it naturally occurs. For example, isolated myofibroblasts are obtained from solid heart leaflet tissue but are separated from other cell types which are present in heart leaflet interstitial tissue. Cells are "isolated" when the particular cell type is at least 60% of a cell population. Preferably, the cells represent at least 75%, more preferably at least 90%, and most preferably at least 99%, of the cell population. Purity is measured by any appropriate standard method, for example, by fluorescence-activated cell sorting (FACS) using cell type-specific markers described herein. A population of cells used to cellularize an acellular valve structure or synthetic structure may be a mixture of two or more different cell types, each of which is isolated. For example, valves are colonized with a mixture of isolated myofibroblasts and isolated endothelial cells. An acellular or decellularized valve is one which is synthetic (not derived from a living organism) or one which has been treated to remove at least 85% of the cells with which it is naturally associated. Preferably, 90%, 95%, 99% or 100% of the cells with which the donor valve is associated in vivo are removed.

The myofibroblasts used to cellularize a valve matrix are obtained from a variety of tissue sources, e.g., cardiac, vascular, or dermal tissue. Preferably, the cells are derived from a human donor. Preferably, the cells are derived from histocompatible (e.g., autologous) mammalian heart leaflet interstitial tissue such as human heart leaflet interstitial tissue. Alternatively, the cells are derived from other tissue sources, e.g., dermal tissue, and cultured under conditions which promote a myofibroblast-like phenotype. The cells are syngeneic with respect to the intended recipient of the replacement valve.

To inhibit dedifferentiation of myofibroblasts, the cells are maintained in the presence of one or more cell signaling or growth factors which favor the leaflet myofibroblast phenotype (i.e., contractile and secretory function). The cells are maintained in static culture conditions or subjected to pulsatile flow culture conditions. Growth factors include basic fibroblast growth factor (bFGF). As is discussed above, the cells are cultured in endothelial cell-conditioned media or in physical contact with endothelial cells. Myofibroblasts may be cultured in the presence of a purified or recombinant growth factor. Preferably, the growth factor is derived from an endothelial cell, e.g., purified from endothelial cell conditioned media. The factor is purified using methods known in the art such as standard chromatographic techniques or recombinant cloning technology. A cell signaling factor is distinguished from a growth factor in that a signaling factor influences phenotype (e.g., secretory or contractile activity) rather than growth rate.

Conditioned media is fractionated by size and charge. The ability of each fraction to promote and maintain the myofibroblast phenotype is assessed using methods known in the art, e.g., qualititative evaluation by immunocytochemistry and histology to measure contractile and synthetic properties and quantitative evaluation using assays for matrix components including collagen, elastin and glycosaminoglycans. Proteins from the fraction(s) with the highest activity are purified and sequences using known methods. A secretory cell, e.g., one that has been genetically modified to produce a signaling factor, a growth factor or matrix component, is used in coculture with isolated myofibroblasts. For example, the secretory cell is of non-endothelial and non-myofibroblast origin.

Myofibroblast cells are cultured under pulsatile flow conditions to enhance production of type I collagen and minimize dedifferentiation. Cellularized valves cultured under such conditions assume the functional anatomy of a native valve. For example, the valve leaflets contain a monolayer of endothelial cells on the external layer and myofibroblasts in the inner layers. The leaflet interstitium contains a non-homogeneous matrix of one or more layers with myofibroblasts present in all layers and with collagen fibrils oriented in more than one direction. The cell culture conditions inhibit apoptosis of a myofibroblast that has been removed from a donor mammal, i.e., a harvested, cultured, transformed or transplanted myofibroblast. The culture method enhances viability and contractile activity of myofibroblasts in vitro.

Also within the invention is a genetically-modified myofibroblast. For example, the fibroblast is genetically modified to confer a myofibroblast phenotype, e.g., matrix synthetic capability, contractile capability The modified fibroblast produces increased levels of collagen I (compared to a normal, untreated fibroblast), fibronectin, or glycosaminoglycans. The cells may also be modified to express recombinant actin and myosin or heparin. Genetically-altered cells which have colonized a replacement heart valve are useful as an in vivo recombinant protein delivery system to deliver therapeutic polypeptides such as anticoagulant or antithrombotic agents.

A method of manufacturing an artificial heart valve includes the steps of (a) providing an acellular matrix, (b) seeding the matrix with isolated myofibroblasts; and (c) culturing the myofibroblasts under actual or biochemically simulated pulsatile flow conditions. Optionally, the matrix is seeded with additional cell types such as endothelial cells and/or secretory cells. The tissue culture media includes growth and cell signaling factors, e.g., those which are present in endothelial cell-conditioned media. Alternatively, factors are isolated from conditioned media, recombinant, or synthetic.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, the preferred methods and materials are described herein. All publications, patent applications, patents, and other references mentioned herein are incorporated by reference in their entirety. In the case of conflict, the present specification, including definitions, will control. In addition, the materials, methods, and examples are illustrative only and are not intended to be limiting.

Other embodiments and features of the invention will be apparent from the following description thereof, and from the claims.

BRIEF DESCRIPTION OF THE DRAWINGS

FIGS. 1A–B are photomicrographs. FIG. 1A shows a native leaflet, and FIG. 1B shows a decellularized leaflet.

FIGS. 4A–H are photomicrographs of cells derived from a tricuspid valve biopsy. FIGS. A–B show cells stained with an antibody specific for alpha smooth muscle actin; FIGS. 4C–D show cells stained with an antibody specific for vimentin; FIGS. 4E–F show cells stained with an antibody specific for fibronectin; and FIGS. 4G–H show cells stained with an antibody specific for chondroitin sulfate. FIGS. 4A, C, E, and G are phase contrast micrographs, and FIGS. 4B, D, F, and H are fluorescent micrographs.

FIGS. 6A–B are photomicrographs of a section of a Photofix bovine pericardium seeded in vitro with myofibroblasts cultured from the sheep tricuspid valve. FIG. 6A is a phase contrast micrograph showing the results of staining with hematoxylin and eosin (myofibroblasts are indicated with an arrow). FIG. 6B is a fluorescent micrograph showing the results of labeling with an anti-vimetin antibody.

DETAILED DESCRIPTION

The presence of viable functional myofibroblast cells in the cardiac valve is essential for leaflet contractility, production of extracellular matrix, and thus for maintenance of proper valve function. Valves devoid of such cells lack the abilities to grow, repair, and remodel. The replacement valve of the invention is a "personal" valve, containing cells derived from histocompatible tissue, such as from the valve recipient patient or neutered non-antigenic cells. The cells dwell within a non-immunogenic acellular matrix support from a donor. The donor valve scaffold is derived from a syngeneic, allogeneic, or xenogeneic donor. The methods are also applicable to matrices other than homografts. Optionally, the scaffold is modified to promote ingrowth and avoid regurgitation. Alternatively, the scaffold is constructed in vitro. Advantages of such a valve include elimination of need for immune suppression when transplanting cells from a donor and elimination of biocompatibility concerns which accompany the use of biomaterials in tissue engineered valves.

For example, an adult or pediatric valve replacement is made which approximates a normal, unstressed native valve, both in terms of numbers and amounts as well as types of cells and matrix. The valve is fully hemodynamically functional, without need for anticoagulation or immunosuppression, with durability extending potentially to the recipient's natural life-span.

The juvenile sheep chronic implant model of heart valve transplantation is an art recognized model for human transplantation. Ten cryopreserved sheep homograft valves and 5 cryopreserved human xenograft valves were transplanted into the pulmonary position of sheep. All were evaluated via ECHO. The data indicate that the homografts were predominantly acellular at 20 weeks. Cell culture of sheep leaflet interstitial cells are cultured as described below and seeded onto valve scaffold. The recellularized valves are evaluated using the sheep model.

Bioprosthetic Valve Components

A structure which acts as a scaffold is colonized by living cells. The scaffold is obtained from a human homograft cardiac valve (either pulmonary or aortic); a xenograft cardiac valve (e.g., porcine or bovine). Alternatively, it is made from a synthetic polymeric material, (e.g., polylactic/polyglycolic acid). The structure is acellular and has the geometry of a native cardiac valve. In the case of the homograft or xenograft valve, cells are removed from the structure using methods known in the art, e.g., as described in U.S. Pat. No. 5,843,182 or WO 96/03093. Acellular human homograft cardiac valves that have been rendered acellular are preferred because of their low antigenicity and similarity to native human valve in geometry and molecular composition. Other compositions such as plastic, metal, or cloth can be used as the valve structure.

Mechanical Properties

The cardiac valve replacement approximates a native mammalian heart valve with regard to hydrodynamics and durability. The valve is strong, opens with a minimal transvalvular pressure gradient, and exhibits minimal regurgitation upon closure. The valve therefore produces a minimal transvalvular pressure gradient, and minimal regurgitation, turbulence, shear stress, stagnation, and resistance to flow. Values for each of the parameters listed above are calculated using methods known in the art. Values for a replacement valve are calculated relative to properties of a native value. Using the properties of a native valve as a baseline, a replacement valve is preferably characterized by numerical values of each property in the range of 5–25% of the native valve measurements (less than 5% being close to ideal). Instruments form Dynatek Dalta (Galena, Mo.) are used to evaluate mechanical properties of a valve.

Fatigue resistance is measured by applying cyclic loading to the valve, and plotting stress versus logarithm of the number of cycles to failure.

A pulse duplicator is used to duplicate physiological flow. A pulsatile pressure gradient corresponding to flows of 2–7 L/min. at 70–160 cycles per minute is applied. Differential pressure transducers, flowmeters, and laser Doppler anemometry instruments are inserted into the path to allow measurement. Transvalvular pressure drop, regurgitation, turbulence, stagnation, and high shear in the flow path are evaluated.

An accelerated life-cycle tester is used to measure wear and fatigue, to assess long term durability. At least 380 million cycles are applied to approximate at least 10 years of life. Physiologic pressure gradients are applied. Scanning electron microscopy is used to evaluate wear depth.

Myofibroblasts and Other Cell Types for Cellularization of Valve Structures

The biological valve is decellularized prior to culture with isolated myofibroblasts. The decellularized valve contains other extracellular matrix components such as collagen which confers upon the valve general tensile strength, proteoglycans which absorb stress, confer flexibility, regulate the extent of collagen fibrils crosslinking, and elastin for leaflet coaptation or valve closure.

Cells e.g., isolated myofibroblasts, are obtained from a donor mammal. Preferably, the mammal is a human, and more preferably, the tissue is obtained by biopsy from the individual to be treated. For example, cells are surgically removed from heart valve tissue, or elsewhere (e.g., artery, vein, dermis). The cells are cultured ex vivo to expand the cells. Alternatively, cells are obtained from human cadaver tissue, cultured to expand cell number, and used to cellularize a valve scaffold.

The scaffold is contacted with cells (e.g., myofibroblasts or myofibroblast-like cells, in the presence or absence of endothelial cells). Replacement valves are colonized with cells in a manner which resembles a naturally-occurring valve. Naturally-occurring cardiac valve leaflets have three internal layers—ventricularis, spongiosa, and fibrosa. Endothelial cells are present in a single layer around the leaflet's blood-contacting surface. Myofibroblasts are found throughout the 3 layers, with the sparsest population in the fibrosa. Myofibroblasts are aligned with the collagen fibrils in the matrix of the valve. The replacement valve, recellularized as described herein, approximates a naturally-occurring valve, as follows. The ventricularis contains myofibroblasts, multidirectionally oriented collagen, and extensive elastin, which is perpendicular to the free edge. The spongiosa contains myofibroblasts, loosely arranged collagen, and proteoglycans, including chondroitin sulfate and hyaluronic acid. The fibrosa contains fewer myofibroblasts than the other layers, a small number of elastic fibers, and dense collagen that is circumferentially oriented, crimped when relaxed, and elongated under pressure.

Cells incorporated within the valve matrix internal layers are myofibroblasts, i.e., the cells have dual biological function: matrix synthesis and contractility. Myofibroblast phenotype is assessed by immunocytochemistry with the following antibodies: monoclonal anti-alpha-smooth muscle actin, monoclonal anti-vimentin, anti-desmin, monoclonal anti-light chain myosin, monoclonal anti-alpha-tubulin, monoclonal anti-cellular fibronectin, monoclonal anti-chondroitin sulfate (SIGMA, St. Louis, Mo.), and monoclonal anti-prolyl-4-hydroxylase (Dako, Carpintera, Calif.). The localization and the ability of the cells to synthesize matrix components are assessed by standard histological methods (e.g., Movat's pentachrome stanin), evaluation of mRNA for collagen type I, collagen type III, and elastin, and by incorporation of proline for collagen and sulfate or glucosamine for proteoglycans.

Endothelial cell phenotype is assessed by immunocytochemistry with antibodies to factor VIII (polyclonal antibody, BioGenex, San Ramon, Calif.) and to CD31 (monoclonal antibody, Dako, Carpintera, Calif.), and by incorporation of DiI-labeled acetylated low density lipoprotein (Biomedical Technologies, Stoughton, Mass.).

The acellular matrix is seeded prior to transplantation with a secretory cell (alone, or in combination with other cell types i.e. myofibroblasts, smooth muscle cells, endothelial cells). These secretory cells (which may be modified genetically prior to transplantation) function to attract autologous cells to migrate into the matrix in vivo after transplantation. The cells secrete signaling and growth factors (such as those derived from endothelial cell-conditioned medium, as described) to attract and maintain the differentiation of autologous cells such as the recipient patient's myofibroblasts and endothelial cells.

Tissue Culture Conditions

Myofibroblasts are harvested from histocompatible donor tissue, e.g., valve leaflets or dermal tissue, and cultured according to known methods, (e.g., Messier et al., 1994, J. Surg. Res. 57:1–21) or by explant culture. For explant culture, leaflets are scraped to remove endothelium and chopped into 1–3 mm3 pieces. Pieces are plated in tissue culture flasks or dishes, and myofibroblasts migrate out within 5–7 days. Fibroblasts from vascular, dermal, or other tissue sources are cultured by the same methods. Fibroblasts from these sources acquire the myofibroblast phenotype with the use of dynamic tissue culture conditions and/or cell signaling factors. Culture medium used to grow and maintain myofibroblast cultures is M199, 5–15% fetal bovine serum, penicillin-streptomycin.

Endothelial cells are cultured according to standard protocols (e.g., Gimbrone, M. A., 1976, Culture of vascular endothelium, Chapter 1 in Spaet, T. (ed.) Progress in hemostasis and thrombosis. Vol. III. Grune and Stratton, Inc., pp. 1–28) from femoral vein or artery, jugular vein or artery, or valve leaflet biopsies. Cultures are generated by scraping endothelium, collagenase treatment (0.1%), or explant cultures. Culture medium is the same as for myofibroblast culture. Alternatively, cells are cultured in serum-free medium with endothelial cell growth factor (Gibco, Gaithersburg, Md.) added to promote proliferation. Collagen or gelatin coating of tissue culture dishes or flasks is optionally used to promote cell attachment.

Mixed cultures of myofibroblasts and endothelial cells are cocultured with cell-cell contact. Cells for coculture are generated by either collagenase treatment or explant culture of unscraped leaflets. Cells are separated into isolated single-type populations by flow cytometry using DiI-Ac-LDL to label endothelial cells.

Cells are cultured in a mixed culture without cell-cell contact, but with free diffusion of soluble factors. For example, myofibroblasts and endothelial cells are separated by a cell culture insert composed of a semipermeable membrane, i.e. cellulose acetate. One cell type is grown on a tissue culture dish, while the other grows on the cell culture insert. Alternatively, the two cell types are grown on opposite sides of a semi-permeable membrane.

Conditioned medium from the co-cultures is collected and separated into fractions by size and by charge using standard protein and proteoglycan column isolation methods. Fractions are analyzed for the ability to promote the myofibroblast phenotype, and for the ability to promote recellularization of valve tissue. Either purified myofibroblast-promoting factor or conditioned media is used to promote growth and dedifferentiation of cells to be used as the cellular component of replacement heart valves.

Cells are typically grown in culture prior to seeding for 1–4 weeks. The cells are maintained under standard static tissue culture conditions, in a bioreactor (with or without rotation), or in a pulsatile flow chamber. Cells cultured in a pulsatile flow chamber are either myofibroblasts or mixed-type populations, e.g., a mixture of isolated myofibroblasts and isolated endothelial cells.

Cells which have been genetically modified to produce specific proteins (i.e. myofibroblast differentiation factors, endothelial cell-myofibroblast cell signaling proteins, extracellular matrix components) are cultured as described above. Stem cells (whose phenotype is not permanently determined) are cultured and driven toward a myofibroblast phenotype through incubation with differentiation factors and/or pulsatile culture conditions.

Endothelial cells are isolated by perfusion of vessels or incubation of valve leaflets with collagenase. Culture medium is changed 30 minutes after the initial culture to remove fibroblasts and smooth muscle cells. Cells are cultured in endothelial basal medium 131 with 10% fetal bovine serum and 2 ng/ml basic fibroblast growth factor. Endothelial cells are identified by their uptake of DiI-labeled acetylated low density lipoprotein (DiI-Ac-LDL).

Leaflet interstitial cells are the preferred source of myofibroblasts. Leaflet tissue is dissected from the central third of coronary cusps, beginning at the nodule of Arantius and ending at a point 3–5 mm from the base. Excised tissue is incubated for 24 h in a 37 degrees C humidified environment with 5% $CO_2$, 95% air in collagenase solution, then aspirated for thorough cell dispersion. Cells are cultured in tissue culture flasks in M199 medium with 10% FBS.

The ability of interstitial cells or isolated myofibroblast cells to contract is assessed using known methods, e.g., Harris et al., 1980, Science 208:177) Cells are cultured on a flexible substrate composed of polydimethyl siloxane. The visible generation of wrinkles on the surface of the rubber reveals cellular contraction.

Methods for seeding the valves include diffusion of cells, dynamic flow conditions, or direct injection. Cells cultured and re-implanted are labeled with a fluorescent tracer prior to implantation, to distinguish between cultured and native cells.

Genetic Modification of Cells for Matrix Seeding

DNA is incorporated into cells using standard recombinant technology. Targeting cell specific vectors are preferred. For long term stable transduction of recombinant DNA encoding polypeptides to be expressed, retroviral vectors, e.g., murine leukemia viruses such as Moloney murine leukemia virus, are used. A cell-specific promoter such as a lysyl oxidase (LOX) promoter (Reynaud et al., 1999, Cellular and Molecular Biol. 45:1237–1247) is used for expression of recombinant proteins in myofibroblasts. Recombinant polypeptides to be expressed in cells of the matrix include at least part of the coding region of the following genes: human bFGF (GENBANK Accession No. M27968 or J04513), human VEGF (GENBANK Accession No. AF092127, AF092125, or M32977), human fibronectin (GENBANK Accession No. M26179), human beta 1 integrin (GENBANK Accession No. L24121 or U31518), human TGF-beta-1 (GENBANK Accession No. J04431), human alpha 1 type I collagen (GENBANK Accession No. U06669), human aortic-type smooth muscle alpha-actin (GENBANK Accession No. M33216), or human myosin light chain 1 (GENBANK Accession No. M20642).

Signalling and Growth Factors

Soluble factors to be delivered to the matrix include members of the families of transforming growth factors (e.g., TGF-beta), fibroblast growth factors (e.g., bFGF), and vascular endothelial growth factors (e.g., VEGF). TGF-beta and bFGF are used to promote myofibroblast growth (Khouw et al., 1999, Biomaterials 20:1815–1822), and VEGF is used to promote angiogenesis. Alpha smooth muscle actin and myosin gene products are used to convert fibroblasts into myofibroblasts. Extracellular matrix factors (fibronectin, collagen, and integrins (a1b1 and a2b1 for collagen, and a5b1 for fibronectin)) are used to promote myofibroblast migration into the valve matrix. Ascorbic acid is used to regulate collagen synthesis using known methods (e.g., Tajima et al., 1982, Biochem. Biophys. Res. Commun. 106:632–7 and Grinnell et al., 1989, Exp. Cell Res. 181:183–191)

Evaluation Of Explanted Valves

The function and durability of replacement valves is evaluated as follows. Once explanted, valves are placed either into formalin or paraformaldehyde for evaluation at the histological, cellular, and molecular levels, into glutaraldehyde for evaluation by transmission electron microscopy, or into tissue culture medium for specific cellular and molecular assays, tissue culture, or mechanical evaluation.

Histology

Valves are sectioned with a cryostat, a microtome, or an ultramicrotome, depending on the evaluation procedure.

Histological stains include hematoxylin and eosin, Miller's elastin stain, Movat's pentachrome stain, and von Kossa stain. Valves are examined for the presence of an intact endothelium and a stroma containing matrix proteins and cells. The presence of elastin, collagen, fibronectin, and glycosaminoglycans are assessed.

Transmission Electron Microscopy (TEM)

Cultured cells and valve sections are examined by TEM for general morphology, cell and matrix types, and cell viability. Cells are examined for the presence of cellular organelles appropriate for contractile and synthetic cell types (i.e. cytoskeletal filaments, endoplasmic reticulum), as well as intercellular communicative junctions.

Mechanical Properties

To monitor calcification, calcium content of explanted valves is assessed via atomic absorption spectroscopy. Evaluation of valve mechanical properties, (e.g., tests for strength, flexibility, low-strain-rate tensile fracture, high-strain-rate extensibility, stress-relaxation, and forced vibration) are carried out using known methods.

Cell and Matrix Properties

Endothelial cell function is assessed by immunocytochemistry for von Willebrand factor, and CD31, as well as by uptake of ac-LDL. Markers of contractile properties include smooth muscle actin and myosin light chain by immunohistochemistry, as well as staining with Texas red-phalloidin, which selectively labels F-actin and has the advantages of stoichiometric binding and negligible non-specific staining. Cytoskeletal markers include vimentin, desmin, and tubulin, by immunohistochemistry. The ability of myofibroblast cells to synthesize fibronectin and chondroitin sulfate proteoglycans and to modify collagen types I and III is determined by immunohistochemistry and in situ hybridization.

The presence of fibronectin, collagen types I and III, and chondroitin sulfate proteoglycans (core proteins as well as glycosaminoglycan chains) is assessed by immunohistochemistry and Western blotting. Collagen levels are evaluated by hydroxyproline assays known in the art, as well as with the Sircol dye assay (Accurate Scientific, Westbury, N.J.).

Seeding of Cells Into Replacement Valve Structure

For seeding purposes, harvested primary cells are cultured and used within culture passages 1–5 to preserve phenotype. Myofibroblasts are seeded to populate a valve structure at cell numbers of 10,000–150,000 per ml. The matrix or valve structure is optionally treated prior to cell seeding to promote cell attachment, and during the seeding process to promote migration into internal layers, proliferation and maintenance of valve cell phenotype. Coating compositions include cell signaling factors, growth factors, and extracellular matrix components that were removed from a donor valve tissue during decellularization. Such matrix components are typically not present in the case of a synthetic polymer valve matrix, or may need to be augmented to facilitate seeding. For example, the structure is coated with basic fibroblast growth factor, platelet derived growth factor, endothelial cell growth factor, fibronectin, integrins, collagen type I, chondroitin sulfate, hyaluronic acid, and heparan sulfate. Factors also include cell signaling and differentiation factors isolated from co-cultures of myofibroblasts and endothelial cells, cultured under pulsatile flow conditions.

The valve scaffold matrix is seeded with myofibroblasts first, followed by endothelial cells. Alternatively, the matrix is seeded with myofibroblasts, then incubated with factors to attract endothelial cells in vivo, or the matrix is seeded with a mixed population of myofibroblasts and endothelial cells. Alternatively, the matrix is modified first mechanically and/or biochemically (e.g., unique packaging and attractant vehicles are used to retain signaling factors in contact with cells during cell growth, migration, and differentiation). For example, the matrix is first incubated with signaling or growth factors prior to the addition of cells such as myofibroblasts and endothelial cells. Alternatively, signaling proteins produced in response to energy dissipation, which regulate increased production of alpha-smooth muscle actin and related contractile compounds, are introduced directly (e.g., by contacting the matrix with a factor) or via a secretory cell (by seeding the matrix with secretory cells expressing the factor) to induce and/or maintain a myofibroblast phenotype.

Once cells have attached (3–24 hours), the recellularized valve matrix is incubated under pulsatile flow conditions designed to duplicate the cyclic opening and closing under pressure of a native valve. Typical flow values approximate a cardiac output of 2–7.5 liters/min, with a frequency of 60–120 cycles/min and resistances configured to duplicate back pressures of up to 120 mm Hg for aortic valve according to standard methods. For example, isolated myofibroblasts (in the presence or absence of endothelials cells) are cultured with a valve structure under normal blood flow conditions. Frequency is 70 bpm with a diastolic pressure of 70 mg Hg and a flow rate of 5 L/min.

Pulsatile flow conditions promote and/or maintain a myofibroblast phenotype. As is discussed above, myofibroblasts are distinguished phenotypically by their content of alpha-smooth muscle actin. Pulsatile flow culture conditions also promote elevated synthesis of Type I collagen by myofibroblasts. Pulsatile flow culture conditions for fibroblasts and myofibroblasts are known in the art, e.g., U.S. Pat. No. 5,899,937.

Methods of Enhancing Type I Collagen Production

Myofibroblasts and/or myofibroblast/endothelial mixtures are cultured as described above to increase type I collagen production relative to type III collagen production. The amount of collagen in the valve leaflet is assessed by using known methods, e.g., the 4-hydroxy-proline assay, and also by the Biocolor Sircol dye assay (Biocolor; Accurate Scientific, Westbury, N.J.). The proportions of collagens type I and III in the valve leaflet is an important measure of the health of the tissue. Collagen III is present in scar tissue or healing tissue, and amounts exceeding 15–20% are not appropriate for a functional valve. Types of collagen are evaluated by interrupted gel electrophoresis and by transmission electron microscopy (TEM).

Interrupted gel electrophoresis resolves type I, III, and V collagen, the main subtypes found in leaflets. After radiolabeling with $^3$H-proline, the tissue is electrophoresed on nonreducing 5% SDS polyacrylamide gel in the presence of 0.05M urea until the dye front has migrated approximately ⅓ of the total run distance. Then 20 microliters of b-mercaptoethanol is added to each well. Since type III collagen is disulfide bonded, its migration is retarded relative to the a chains of type I and V collagen until the reducing agent is added. Therefore, the a1(III) chain can be resolved from the a1(I) chain. The a1(V) and a2(V) chains migrate between the a1(I) and the a1(III) chains. The gel is soaked in 10 volumes of sodium salicylate (pH 6.0) for 30 min to enhance 3H emission intensity and exposed to Kodak SB X-ray film for fluorography. The ratio of type III to type I collagen will be determined by scanning densitometry. Type I and type III collagen are distinguished as follows: collagen I fibrils are 50–100 nm in diameter, and collagen III fibrils are 25–40 nm (analyzed by TEM). For example, the ratio of collagen is I:III:V=85:15:5. Orientation of collagen fibrils varies, e.g., crimped vs. elongated, depending on layer and pressure conditions. Collagen crosslinking is evaluated for extent of crosslinking and type of crosslinking (reducible vs. non-reducible, typical of load-bearing tissues).

Quantification of Collagen

Tissue is homogenized in the presence of protease inhibitors. Quantity of collagen is measured using a standard 4-hydroxyproline assay. Alternatively, collagen content is quantified using the Sircol dye binding assay (Biocolor, Accurate Scientific, Westbury, N.J.) Th Sircol dye contains Sirius Red, an anionic dye with sulphonic acid side chain groups. These groups react with side chain groups of the basic amino acids present in collagen. Binding is highly specific because, under the assay conditions, elongated dye molecules become aligned in parallel with long, rigid, helical structure of collagen.

RNA Analysis of Collagen

Collagen content is measured by detecting collagen gene transcripts or the gene product itself.

A cDNA probe for collagen type I is subcloned into a transcribable vector, e.g., pGEM7Z (insert: Hf677, site I: EcoR1; site II: EcorR1). Competent $E.\ coli$ are transformed and replicated in culture to produce additional plasmid and inserts.

The probe is labeled with a detectable marker using standard methods. For example, the probe is labeled with digoxigenin-II-UTP, and the labeled double stranded DNAs are generated with using a random priming reaction. In vitro transcription of DNA is used to synthesize labeled RNA probes, both antisense and sense (via SP6 and T7 RNA polymerase promoters in the pGEM7Z plasmid).

For Northern analysis of collagen transcripts, total RNA is isolated from native cardiac valves and from cultured cells using methods known in the art (e.g., by a SDS lysis/acid phenol technique. RNA is separated by electrophoresis on a 1% agarose-formaldehyde gel, blotted onto a charged nylon membrane, and hybridized with the collagen I cDNA probe described above. After high stringency washes, the blots are reacted with an anti-digoxigenin antibody, alkaline phosphatase, and BCIP/NBT. Blots are analyzed by scanning densitometry.

In situ hybridization is also used to measure collagen content. Cells to be analyzed (e.g., cultured cells, genetically-modified cells, or cryosections of valve tissue) are plated or mounted onto slides under RNAse-free conditions. The cells or tissue sections are tixed with 4% paraformaldehyde. Prehybridization is carried out at 37 degrees in a solution containing formamide, Ficoll, polyvinylpyrrolidone, bovine serum albumin, EDTA, salmon sperm DNA, yeast tRNA, and beta-mercaptoethanol) to block nonspecific binding. Both cDNA probes and RNA probes are used for hybridization to optimize mRNA detection. The slides are washed under high stringency wash conditions, and the transcripts detected as described above for Northern blot analysis.

Quantification of Calcium

Atomic absorption spectroscopy is used for elemental determination of calcium.

Juvenile Sheep Model of for Human Aortic Valve Replacement.

Domestic sheep (Ovis aries): Rambouillet, Dorset, Hampshire, Suffolk Breed mix (30, 6 per valve type) either male or female (20 to 40 weeks of age with body weight 40–50 kg) are commercially available. Prior to implantation, the animals are certified to be free from disease.

The sheep is given Amikacin (10 mg/kg IM) and amoxicillin (5–10 mg/kg IM) and fasted from its daily standardized diet from the evening prior to surgery. On the morning of surgery, the animal is weighed, surgical sites are sheared, and the animal is anesthetized with using standard methods.

The sheep is secured to the operating table in the left side up lateral position. Total volume is maintained at 10 ml/kg body weight of 99% oxygen with a 50–100 m. compensation for dead space at a rate of 12–14 cycles per minute (ABG's checked at 15 minutes–30 minutes). Left thoracotomy is performed and the chest entered through the fifth intercostal space. A bypass Heparin bonded shunt is inserted from the right atrium to the distal pulmonary artery with a roller pump head in the circuit. The pulmonary artery is mobilized and a vascular clamp is applied just proximal to the bifurcation and below the level of the insertion of the inflow shunt tubing from the roller pump. The native pulmonary valve is excised with the right ventricle being kept empty as a consequence of the right heart bypass circuit as described above. The tissue engineered valve or control is sutured as an interposition graft. The proximal and distal end-to-end anastomoses is accomplished with running 4–0 Prolene suture. The bypass shunt is occluded and the vascular clamps removed. The homograft or unstented bioprosthesis is oriented with the base closest to the heart to ensure antegrade flow through the graft.

Fresh valves are harvested from one sheep and implanted into another sheep. Valves to be frozen are harvested from an abbatoir as a byproduct of meat packing. They are treated with antibiotics, antifungal agents and cryopreserved. No disease transmission has ever been documented following such treatment. Decellularized valves is carried out using methods known in the art.

Native pulmonary valves are explanted, placed in sterile tissue culture media, and transported in a sealed, autoclaved container to the site of the surgery.

Following implantation and prior to closing, the thoracic cavity is lavaged with warm saline. The fluid from the thoracic cavity is evacuated. The pericardium is closed with Vicryl sutures. The ribs are approximated with Vicryl sutures. The muscle and fascia layers of the chest are approximated with Vicryl sutures (running). The air and blood are evacuated from the thoracic cavity via chest tube. The skin layer of the chest is closed with 2–0 Vicryl subcuticular suture. When the animal is able to breath spontaneously, mechanical ventilation is discontinued and supplemental oxygen substituted.

The animal is placed in the position of sternal recumbency in intensive care. To permit the expulsion of ruminal gas, this position is maintained until the animal regains consciousness. The chest tube is aspirated regularly following the operation and is removed 6 hours after surgery. The animal is awakened with the assistance of a sling and then walked into a pen. Animals receive weekly trans-thoracic ECHO evaluations. Trans-thoracic Doppler echocardiography will be performed weekly to assess for stenosis or regurgitation. Euthanasia is by overdose of pentobarbitol (360 mg/kg).

EXAMPLE 1

Tricuspid Valve as a Source of Cells for Tissue-engineered Cardiac Valve Replacement Cardiac valve replacements are designed to be non-obstructive when open, competent when closed, nonthrombogenic, non-immunogenic, free from calcification, durable, flexible, and strong. Pevious cardiac valve replacements, which are devoid of cells, lack the ability to grow, repair, and remodel as a native valve. Long term growth, repair, and remodeling functions are especially crucial for pediatric patients. The tissue-engineered valve replacements described herein are capable of such functions. The replacements are living valves, containing cells derived from the patient, dwelling within a non-immunogenic acellular matrix support from a donor. Such valves eliminate the need for immune suppression. In addition, the donor valve provides an inherently biocompatible, heterogeneous matrix for optimal support of the patient's own cells.

Figure 1A:
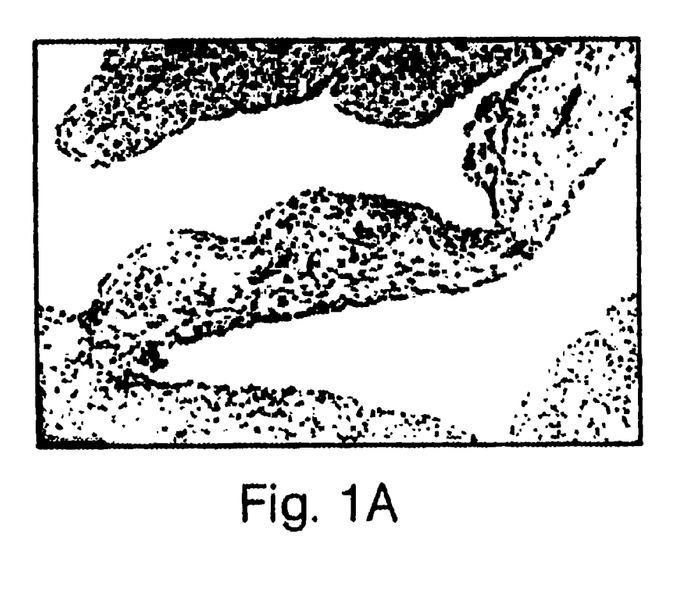
Figure 1B:
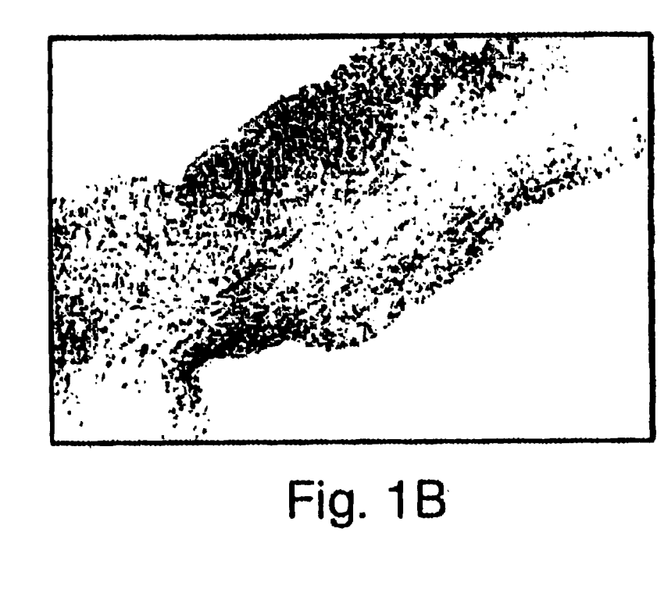

To design the tissue engineered valve replacement, donor cells are removed from a cadaveric donor homograft valve. Decellularization successfully removes greater than 90% leaflet cells from valve leaflets (FIGS. 1A–B). The decellularized homograft valve is repopulated using cells from the patient. An optimal source of autologous cells for repopulation is the tricuspid valve.

Using the juvenile sheep models, a technique that reliably and safely biopsies the tricuspid valve was developed. The same techniques is used to obtain patient cells to be used for repopulation of a decellularized donor valve. Biopsies of the tricuspid valve were cultured and evaluated as sources of cells for valve repopulation. The tricuspid valve was accessible for biopsy under ECHO guidance, with excellent animal survival. Post-operative ECHO revealed no detectable effect on leaflet function. Enzymatic digestion of biopsied tissue gave rise to endothelial cells identified by uptake of DiI-acetylated low density lipoprotein, and myofibroblasts identified by immunoreactivity for smooth muscle actin, chondroitin sulfate, vimentin, and fibronectin. These cells were expanded in culture and banked for future use. The data indicate that tricuspid leaflet cells provide an effective source of autologous cells for recellularization of a decellularized homograft cardiac valve and production of a tissue engineered valve replacement.

EXAMPLE 2

Cell Harvest and Repopulation

A decellularized matrix was obtained by removing donor cells from a homograft valve. The matrix was repopulated with cells from the intended replacement valve recipient. Since the repopulating cells are autologous, the valve resists immunogenic destruction. The anatomy and physiology are essentially identical to the native valve. There is little or no need for anticoagulation.

The valve replacement requires a reliable source of cardiac valve leaflet cells. Interstitial cells are harvested from the recipient yielding an adequate supply of cells for repopulation of the graft. Interstitial cells are safely obtained from the recipient's tricuspid valve. The valve is accessible and contains the cells of interest. Expansion of the harvested cells in culture is possible and provides an ideal source of leaflet interstitial cells.

Surgical methods were carried out using standard protocols. Ten sheep were studied: nine female sheep and one male. The ages of the animals varied from 20 to 60 weeks and their weights varied from 30 to 60 kilograms. At the time of surgery, each animal was sedated, intubated and anesthetized. The animal was placed into the left side down position and the right neck was shaved. Trans-thoracic ECHO was performed to document normal anatomy and physiology. The animal was then transferred to the operating suite where appropriate monitors, including pulse oximetry and electrocardiography (EKG), were placed. A standard Betadine prep was performed and the animal was sterilely draped. A small incision was made in the right neck overlying the carotid sheath. The tissues were divided until the carotid artery and internal jugular (IJ) vein were identified. The IJ was encircled with a vessel loop both proximally and distally. A small venotomy was performed and a 0.8 cm gastrointestinal biopsy forceps was inserted into the vein. The forceps was advanced until resistance was felt. At this point, ECHO was used to identify the tricuspid valve. In some cases, the forceps was visualized as it was advanced, but in most cases it was not. The biopsy was taken by advancing the forceps with closed jaws just past the point of resistance. This was considered to be the passage through the tricuspid valve. The jaws were opened and closed and the forceps were pulled back. In the cases where ECHO was available, tethering of the tricuspid valve was seen as the forceps were pulled back. As the instrument was brought back up through the venotomy, hemostasis was maintained. Three to six biopsies were taken from each animal. The pieces were grossly evaluated, held in sterile media and placed into cell culture. Once adequate specimens were obtained, the venotomy was repaired with a continuous 4–0 Prolene and the incision was closed. Anesthesia was discontinued and the animal was allowed to recover. At the time of explantation, an ECHO was performed. The animal was then euthanized with an overdose of pentabarbitol. The heart was harvested and examined.

Cell culture was carried out using standard methods. Each biopsy piece was incubated for two hours at 37° C. in 1.6% collagenase solution. Digested tissue was pelleted, resuspended and cultured in a single well of a 24-well tissue culture flask. The media was changed every three to five days. When approximately 85% confluence was achieved, the cells were subcultured by incubation with 0.25% trypsin-EDTA at 37° C. for 10–15 minutes. For immunocytochemistry, cells were fixed in 4% paraformaldehyde for 20 minutes, rinsed in 0.1M phosphate buffered saline (PBS), and incubated with primary antibody overnight at 4C. Primary antibodies were diluted 1:100 for alpha smooth muscle actin and vimentin, 1:400 for chondroitin sulfate, in 0.2% Triton X-100, 5% normal goat serum in PBS. Cells were rinsed with 0.2% Triton X-100 and incubated with rhodamine or fluorescein-conjugated goat anti-mouse antibody diluted 1:200 in PBS.

The animals were sacrificed at several different time points. One animal expired during the immediate post-operative period. After four biopsies were performed, the anesthesia was turned off and the animal was allowed to wake up. There was a delay in extubation secondary to poor respiratory effort, although oxygen saturation remained good at over 90% and EKG tracings were normal. The animal was arousable, but had a decreased level of consciousness and labored breathing. Three hours after extubation the animal expired. Upon necropsy, it was noted that the cordae tendineae had ruptured. The posterior leaflet was destroyed and the valve was obviously incompetent.

Two animals were sacrificed acutely to demonstrate that the tricuspid valve was indeed the cardiac tissue that was being biopsied. During these two procedures, the biopsy forceps was advanced until resistance was met. At this position it was sutured in place and left in situ. The animal was euthanized and a right thoracotomy was performed. Necropsy was performed with the biopsy forceps in place. In both cases, biopsy of the tricuspid valve was demonstrated. The posterior leaflet was noted to be between the jaws of the forceps. There was no evidence of deviation of the instrument into the atrial appendage. The other five animals were survived for either 4 weeks (n=3), 5 weeks (n=1) or 15 weeks (n=1). Prior to sacrifice each animal underwent ECHO. All animals demonstrated normal anatomy and function of the tricuspid valve. There was no evidence of regurgitation through this valve and the valvular apparatus was intact. After the animal was euthanized, the hearts were explanted and examined. All five of these animals demonstrated normal anatomy. There was no discontinuity of the tricuspid valve leaflets. No thickening or scarring was noted. The cordae tendinae were normal and there was no evidence to suggest that the endocardium had been disrupted or biopsied.

Figure 5:
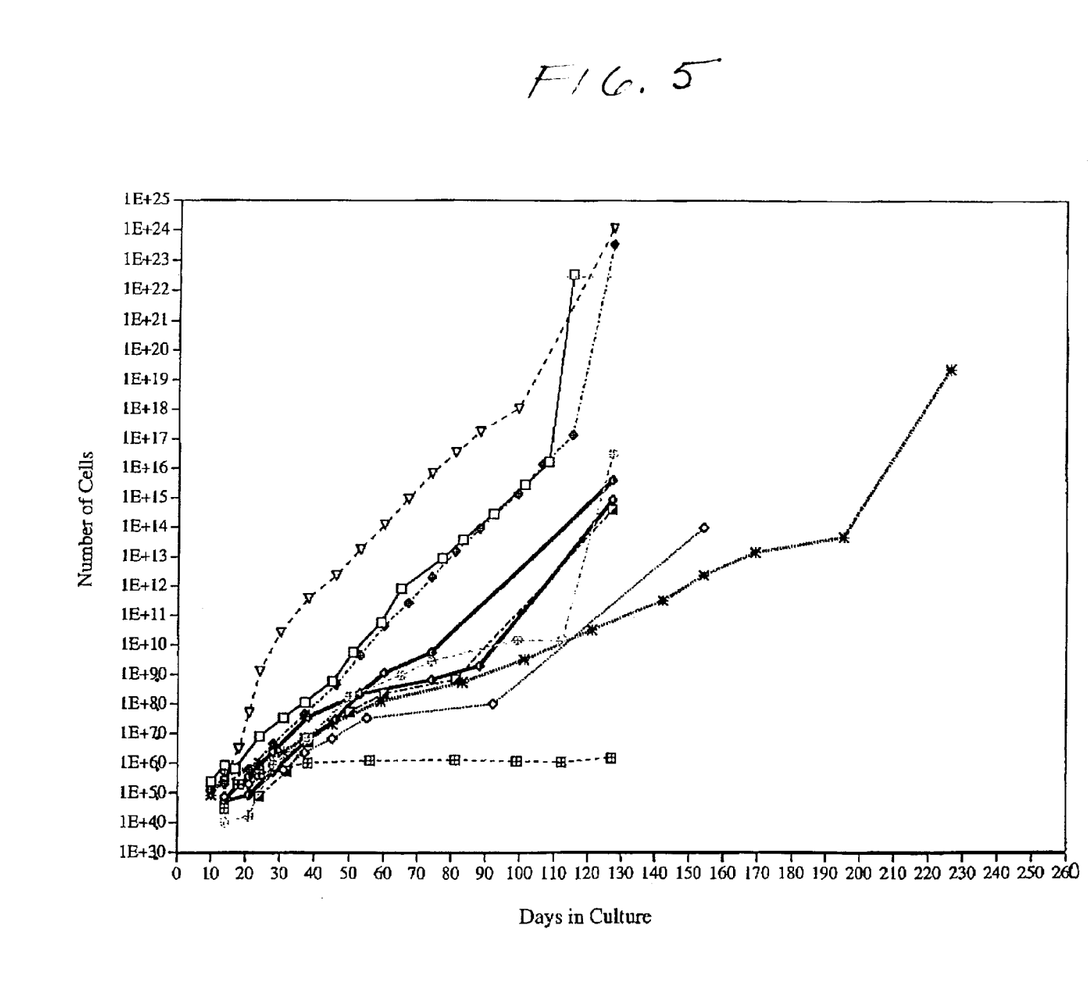
FIG. 5 is a line graph showing cell proliferation of cells derived from a tricuspid valve biopsy.

Collagenase digestion of the biopsy pieces yielded cells that were expanded through at least 5 passages. Growth curves demonstrated varied growth rates, dependent upon biopsy size and plating density (FIG. 5). Cells exhibited a typical myofibroblast morphology and stained positive for alpha smooth muscle actin, fibronectin, vimentin, and chondroitin sulfate (FIGS. 4A–H).

These data indicate successful harvesting of leaflet interstitial cells (e.g., myofibroblasts) from the prospective recipient's tricuspid valve. The procedure is simple, safe and reliable. Under controlled circumstances it is done with sedation and local anesthetic. With the aid of ECHO, the procedure was visualized so that the tricuspid valve leaflet can be biopsied under guidance. Visualization makes the procedure safer by eliminating the complication of biopsying the cordae tendinae and disrupting the valvular apparatus. Up to 15 weeks from the time of biopsy, there were no changes in leaflet integrity and subsequent cardiac function.

The myofibroblast cells that are grown in culture exhibit a normal growth pattern. A single biopsy specimen of approximately 0.8 cm can be expanded to on the order of 75 million cells after two months in culture. Immunohistochemistry with markers for contractile and synthetic properties demonstrates the presence of myofibroblasts through at least ten passages.

Biopsy of the tricuspid valve is an effective method for obtaining recipient cardiac valve leaflet cells. The biopsy of the leaflet itself does not compromise function and animal survival is good. Interstitial cells can be harvested and expanded in culture. The technique described herein is safe and reliable and is an ideal source for harvesting leaflet cells that will later be used to populate a heart valve scaffold.

EXAMPLE 3

In vitro Seeding of Photofix Bovine Pericardium

Sheets of Photofix bovine pericardium (Sulzer Carbomedics) were seeded in vitro with myofibroblasts cultured from the sheep tricuspid valve. Cells from passages 7–9 were placed onto the surface of the Photofix material (approx. 7 mm×5 mm), which was cultured on a Transwell cell culture insert. The seeded Photofix pieces were cultured for 2–6 weeks in vitro in M199 media with 10% fetal bovine serum at 37° C. in a humidified tissue culture incubator with 5% $CO_2$.

Figure 6A:
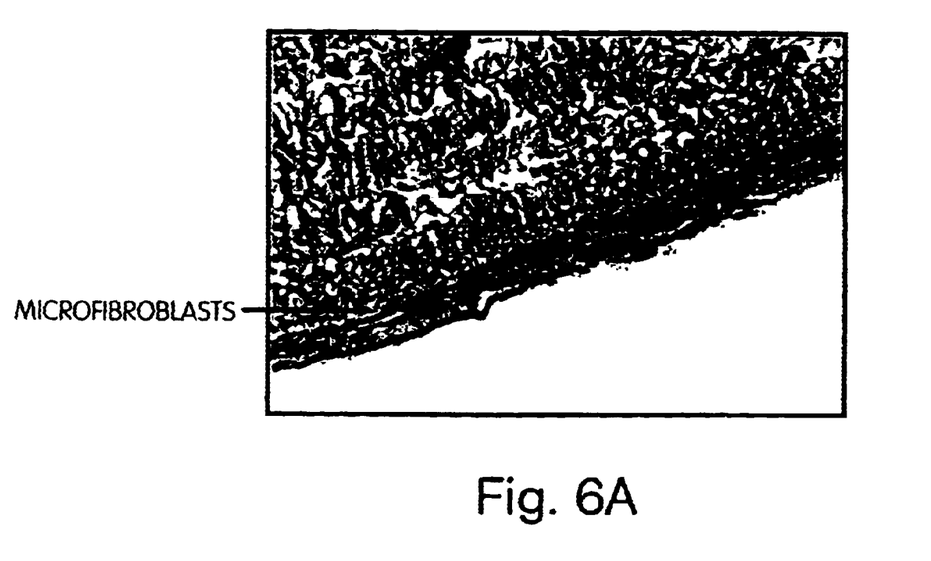
Figure 6B:
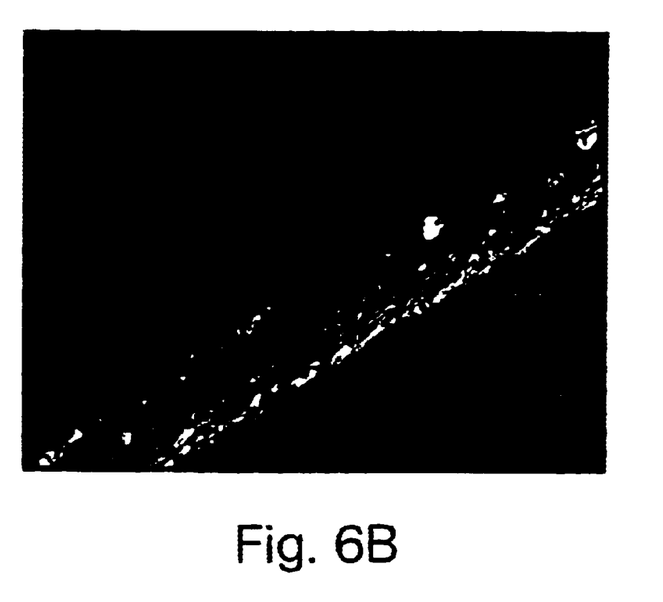

Hematoxylin and eosin staining revealed the presence of up to 5 layers of cells on top of the seeded Photofix material, with cellular infiltration of the middle layers of tissue in some cases. Cells were found to be immunoreactive for alpha smooth muscle actin and vimentin (FIGS. 6A–B).

EXAMPLE 4

Evaluation of Valve Conduits: A Comparison of Cryopreserved Sheep Pulmonary Valve Allografts and Human Cryopreserved Aortic Valve Xenografts An animal model was used to evaluate the suitability of implanting a cryopreserved allograft or xenograft interposed in the pulmonary artery. The art-recognized model described above was used for the evaluation of biological valves and emerging tissue engineered valve designs. To assess the suitability of this model the following items were considered: 1) the ability to assess the surgical handling characteristics of an investigational valve conduit; 2) the ability to evaluate hemodynamic performance using ECHO; 3) postoperative survival for 20 weeks without somatic growth compromising valve conduit performance; 4) no anticoagulation or antiplatelet medications required, and 5) the ability to assess valve conduit related pathology. The model was evaluated using sheep cryopreserved pulmonary valve allografts and human cryopreserved aortic valve xenografts.

The cryopreservation, thawing and washing techniques were identical to those utilized clinically. Under general anesthesia, 15 sheep, Ovis Aries, 20–40 weeks, 40–50 kg, underwent a left thoracotomy. Cardiopulmonary bypass was initiated, native leaflets were removed and the cryopreserved pulmonary valve allograft (n=10) or the human cryopreserved aortic valve xenograft (n=5) was interposed in the pulmonary artery. Transesophageal ECHO studies were conducted on a weekly basis throughout the study. After 20 weeks the animals were sacrificed, the valve grafts were explanted and histologic studies were conducted.

All 15 animals survived for the duration of the study. All animals gained weight during the course of the study. There were no anatomic constraints or surgical handling characteristics that confounded the implantation of these grafts. After 20 weeks of implantation the following hemodynamic findings were observed: 1) mean transvalvular gradients for the allografts were 1.36 mm Hg at 2 weeks and 1.56 mm Hg at 20 weeks 2) mean transvalvular gradients for the xenografts were 1.38 mm Hg at 2 weeks and 1.89 mm Hg at 20 weeks 3) regurgitation was not present in either graft type. Mononuclear cells, histologically resembling histiocytes, were present only within the xenograft cuspal tissue. Histologic studies of both types of valves demonstrated: the loss of cuspal cells and trilaminar architecture, calcification limited to the arterial wall, fibrous sheath formation with endothelialization (primarily on the inflow aspect of the cusps), no endothelial cells present on the cuspal surfaces, and the absence of valve-related thrombosis, cuspal perforations or tears.

These data demonstrate that the interposition of a cryopreserved allograft or xenograft in the pulmonary artery position is feasible in sheep and demonstrates excellent animal survival. The findings also indicate that it is possible to assess surgical handling characteristics of biological valves, long-term hemodynamic performance and valve-related pathology in this animal model. Twenty weeks of implantation, histological evaluation indicated that cryopreserved grafts remain largely acellular with calcium deposition noted to be limited to the graft wall.

EXAMPLE 5

Assessment of a Decellularized Sheep Pulmonary Valve Homograft in vivo

A pulmonary valve homograft was harvested from a juvenile sheep, stored in Lactated Ringers' solution, and decellularized as described above. The decellularized homograft was stored in a humidified tissue culture incubator with 5% $CO_2$ for 47 days prior to implantation. Standard tissue culture media, e.g., M199 media, was changed every 1–2 days for the first 15 days, then once per week for the next 21 days. The homograft was then stored in Lactated Ringers solution, with weekly changes until implantation. The homograft was implanted into the pulmonary position using standard surgical procedures.

ECHO at 7 and 17 days following implantation showed normal hemodynamic function. The homograft was explanted at 17 days following implantation and fixed in Macdowell Trump fixative. Histologic evaluation was carried out using known methods.

Figure 2:
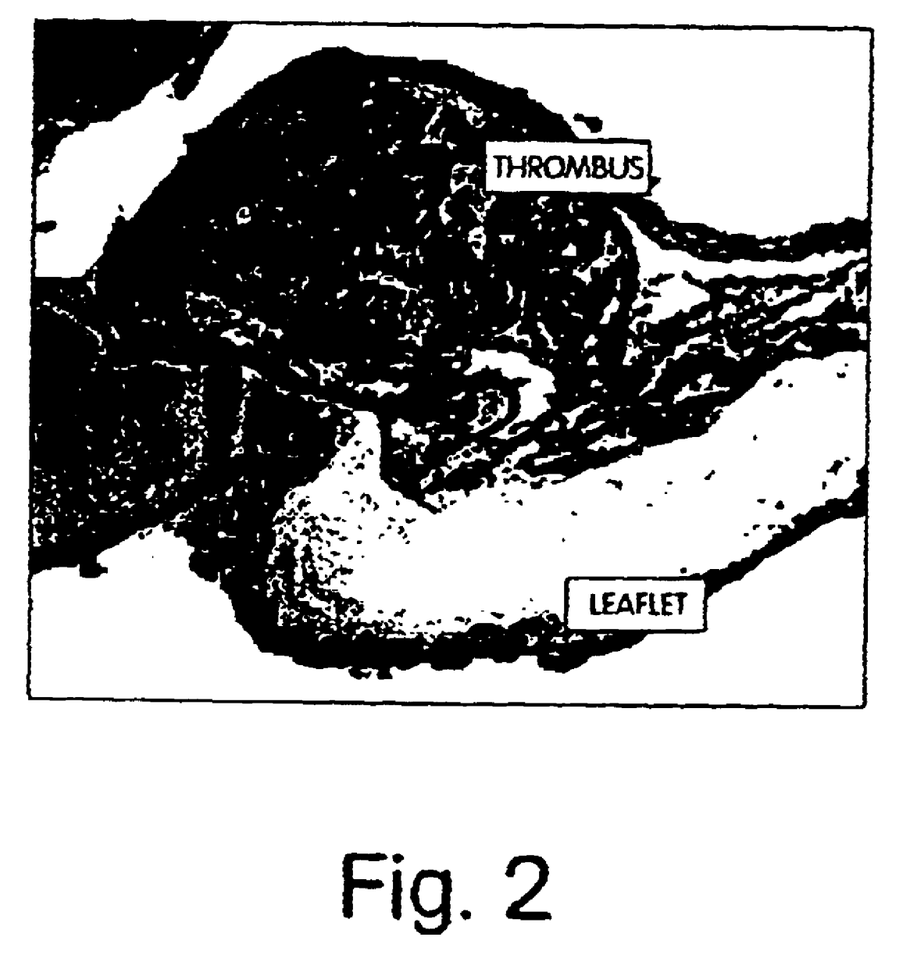
FIG. 2 is a photomicrograph showing a decellularized pulmonary valve 17 days after implantation showing the cusp region of the valve. Loss of trilaminar histologic appearance is typical of semilunar valves. Organizing thrombus is labeled on the outflow surface of the cusp. Fibrin deposition was seen on the inflow surface of the cusp as well as fibrin insudation into the ventricuaris and spongiosa. There was no evidence of host cell infiltration into the cusp. Movat pentachrome stain (100×).
Figure 3:
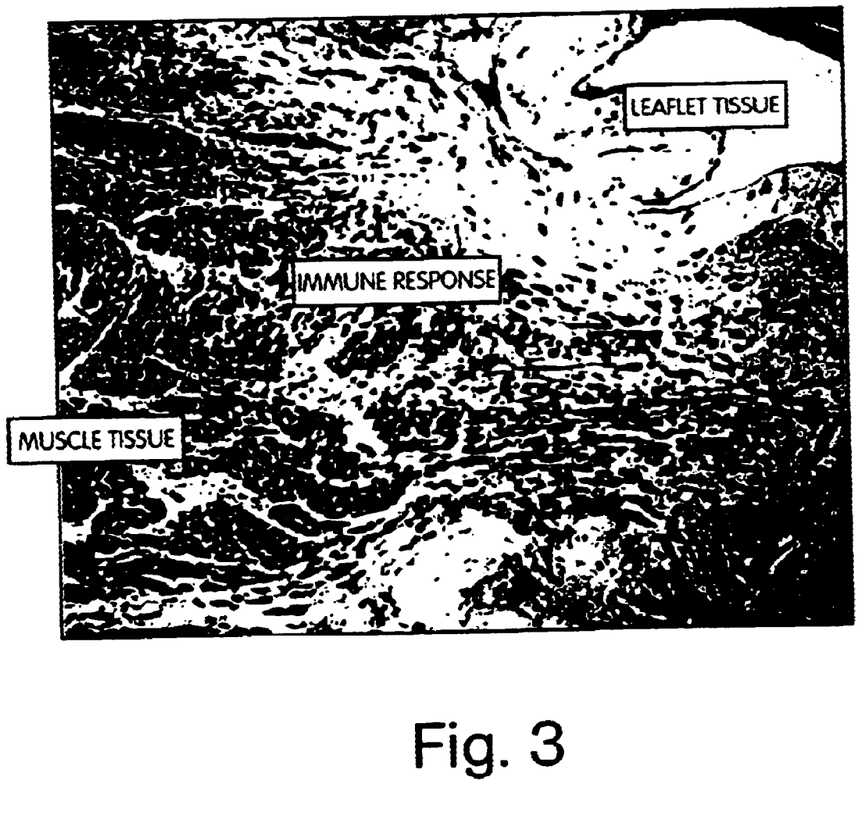
FIG. 3 is a photomicrograph of a decellularized pulmonary valve homograft 17 days after implantation showing the basal region of the valve. Residual cardiac myocytes have elicited an immune response as demonstrated by the presence of plasma cells, mononuclear cells, and macrophages at the site of the residual cells. Movat pentachrome stain (100×).
Figure 4A:
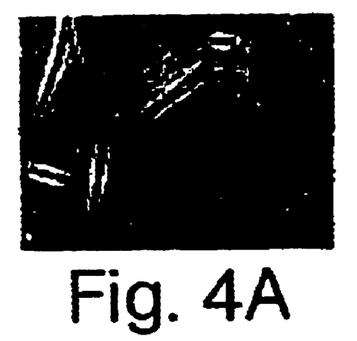
Figure 4B:
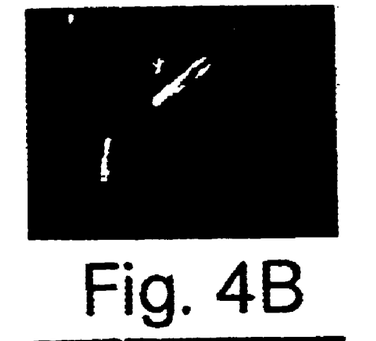
Figure 4C:
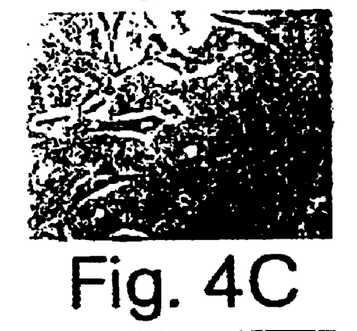
Figure 4D:
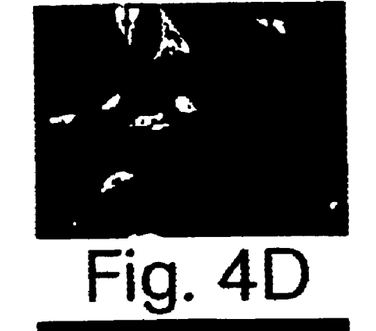
Figure 4E:
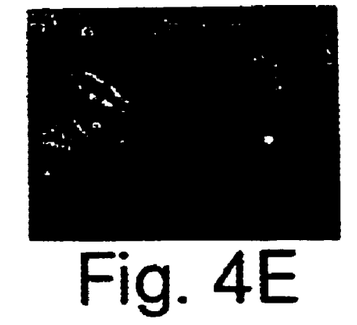
Figure 4F:
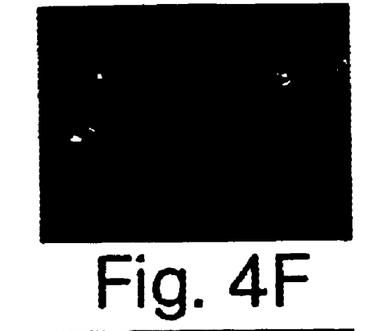
Figure 4G:
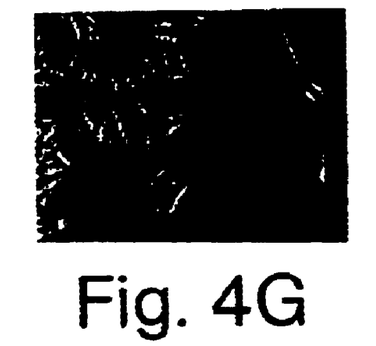
Figure 4H:
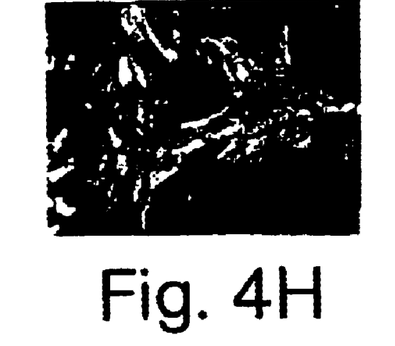

With respect to leaflets, trilaminar structure was reduced or gone. FIG. 2 shows the trilaminar histologic appearance of a decellularized pulmonary valve homograft, and FIG. 3 shows the appearance of the basal region of a decellularized valve 17 days after transplantation. The matrix was acellular but collagen crimp was preserved. Outflow surface of the leaflet had adherent thrombus formation. Inflow surface of the leaflets had eosinophilic fibrin infiltration. The opened spaces that had been seen in in vitro decellularized valve tissue were not apparent in the explanted valve, suggesting compression of these spaces and/or occupation of portions of the spaces by the fibrin.

The pulmonary wall was examined and found to be acellular. There was fibrous connective tissue outside and a capsule or bursa formation. Myofibroblasts were present as detected by various myofibroblast markers (FIGS. 4A–H). There was no giant cell formation or evidence of macrophage inflammatory response.

Basal region of the cusp was also evaluated. In the region of the cusp, there were a few donor cardiomyocytes retained. In contrast to the more mechanical response to the pulmonary artery wall, these residual donor cells invoked a positive cellular inflammatory response. These data suggests that retained cellular material invokes an immune response.

These data indicate that decellularization obviates the immune response. The process of decellularization described herein is reliable and effective in removing cells and cellular debris from donor valves. Some of the mechanical changes seen in vitro in the unloaded valve leaflet were reversed by exposure to loading conditions in vivo. The fibrin infiltration from the ventricularis side suggests that pore size is being maintained and that there are pathways for infiltration of viable myofibroblasts in vivo. Presence of pores and pathways for infiltration allow effective in vitro recellularization of valves.

While the collagen was not viewed as foreign protein, it did engender a sterile capsule or bursa type of response. Despite the significant changes in the fibrous connective tissue, collagen crimp was preserved. The fibrin infiltration suggested that there are pathways for inserting cells. The decellularization process does not obliterate a positive inflammatory response to any residual cellular debris. The thrombus formation in the outflow surface suggested that the collagen is viewed as inert, but nevertheless thrombogenic, suggesting that anticoagulation should be maintained until recellularization has been completed and stabilized.

Other embodiments are within the following claims.

What is claimed is:

1. A bioprosthetic heart valve comprising an acellular matrix, isolated myofibroblasts, and isolated endothelial cells, wherein at least 60% of the total collagen produced by said myofibroblasts is type I collagen.

2. The valve of claim 1, wherein said myofibroblasts produce at least 2-fold greater type I collagen compared to type III collagen.

3. The valve of claim 1, wherein said myofibroblasts produce one or more extracellular matrix components selected from the group consisting of fibronectin, elastin, and glycosaminoglycan.

4. The valve of claim 3, wherein said glycosaminoglycan is chondroitin sulfate or hyaluronic acid.

5. The valve of claim 1, wherein an external layer of said valve comprises a monolayer of said endothelial cells and wherein an inner layer comprises said isolated myofibroblasts.

6. A valve comprising an acellular matrix, isolated myofibroblasts, and isolated endothelial cells, wherein less than 25% of total collagen production by said myofibroblasts is type III collagen.

7. The valve of claim 5, wherein less than 20% of total collagen production by said myofibroblast is type III collagen.

8. The valve of claim 5, wherein less than 15% of total collagen production by said myofibroblast is type III collagen.

9. The valve of claim 5, wherein said myofibroblast is derived from mammalian heart leaflet interstitial tissue.

10. The valve of claim 5, wherein said myofibroblasts is derived from a mammalian vascular or dermal tissue.

11. The valve of claim 5, wherein said myofibroblasts is derived from human heart leaflet interstitial tissue.

12. The valve of claim 5, wherein an external layer of said valve comprises a monolayer of said endothelial cells and wherein an inner layer comprises said isolated myofibroblasts.

13. A bioprosthetic heart valve comprising isolated myofibroblasts, wherein said myofibroblasts are genetically altered to increase type I collagen production relative to type III collagen production.

* * * * *